United States Patent
Grutman et al.

(10) Patent No.: US 11,556,012 B2
(45) Date of Patent: Jan. 17, 2023

(54) SPECTACLES WITH ELECTRICALLY-TUNABLE LENSES CONTROLLABLE BY AN EXTERNAL SYSTEM

(71) Applicant: OPTICA AMUKA (A.A.) LTD., Petach Tikva (IL)

(72) Inventors: Itamar Haim Grutman, Mazkeret Batya (IL); Alex Alon, Binyamina (IL); Yariv Haddad, Raanana (IL); Yoav Yadin, Ganey Tikva (IL)

(73) Assignee: OPTICA AMUKA (A.A.) LTD., Petach Tikva (IL)

( * ) Notice: Subject to any disclaimer, the term of this patent is extended or adjusted under 35 U.S.C. 154(b) by 358 days.

(21) Appl. No.: 16/648,695

(22) PCT Filed: Oct. 10, 2018

(86) PCT No.: PCT/IB2018/057841
§ 371 (c)(1),
(2) Date: Mar. 19, 2020

(87) PCT Pub. No.: WO2019/077442
PCT Pub. Date: Apr. 25, 2019

(65) Prior Publication Data
US 2020/0285062 A1 Sep. 10, 2020

Related U.S. Application Data (60) Provisional application No. 62/572,585, filed on Oct. 16, 2017.

(51) Int. Cl.
  *G02B 27/01* (2006.01)
  *A61B 3/04* (2006.01)
  (Continued)

(52) U.S. Cl.
  CPC .......... *G02B 27/0179* (2013.01); *A61B 3/04* (2013.01); *A61B 3/09* (2013.01); *A61H 5/00* (2013.01);
  (Continued)

(58) Field of Classification Search
  CPC ...... G02C 7/083; G02F 1/294; G02B 27/0179
  See application file for complete search history.

(56) References Cited

U.S. PATENT DOCUMENTS

| 3,580,661 A | 5/1971 | Cooper, Jr. et al. |
| 3,881,921 A | 5/1975 | Frank |

(Continued)

FOREIGN PATENT DOCUMENTS

| CN | 201752480 U | 3/2011 |
| CN | 102253563 A | 11/2011 |

(Continued)

OTHER PUBLICATIONS

Sensomotoric Instruments GMBH, "SMI Eye Tracking Glasses-Discover What is Seen", pp. 1-2, 2011.

(Continued)

*Primary Examiner* — Yuzhen Shen
(74) *Attorney, Agent, or Firm* — Kligler & Associates Patent Attorneys Ltd (57) ABSTRACT

A system for controlling at least one focus aspect of adaptive spectacles (10) having at least one electrically-tunable lens (22), the system including a housing (14), which is physically separate from adaptive spectacles (10), a display screen (16) mounted in housing (14), a sensor (19) mounted in housing (14) and configured to detect a relative position of adaptive spectacles (10) with respect to display screen (16), an interface (17) configured to communicate with adaptive spectacles (10), and a controller (15) configured to receive an input signal from sensor (19), the input signal being (Continued)

indicative of the relative position of adaptive spectacles (10) with respect to display screen (16) and output, in response to the input signal, a command signal for sending to adaptive spectacles (10) via interface (17) to adjust the at least one focus aspect of the at least one electrically-tunable lens (22).

45 Claims, 4 Drawing Sheets (51) Int. Cl.
  *A61B 3/09* (2006.01)
  *A61H 5/00* (2006.01)
  *G02C 7/08* (2006.01)
  *G02C 11/00* (2006.01)
  *G02F 1/29* (2006.01)
  *G06F 3/01* (2006.01)
(52) U.S. Cl.
  CPC .............. *G02C 7/083* (2013.01); *G02C 11/10* (2013.01); *G02F 1/29* (2013.01); *G06F 3/013* (2013.01); *G02B 2027/0178* (2013.01); *G02B 2027/0185* (2013.01); *G02B 2027/0187* (2013.01); *G02F 1/294* (2021.01)

(56) References Cited

U.S. PATENT DOCUMENTS

| | | | |
|---|---|---|---|
| 4,190,330 | A | 2/1980 | Berreman et al. |
| 4,300,818 | A | 11/1981 | Schachar |
| 4,584,592 | A | 4/1986 | Tuan et al. |
| 4,853,764 | A | 8/1989 | Sutter |
| 5,073,021 | A | 12/1991 | Marron |
| 5,212,583 | A | 5/1993 | Vali et al. |
| 5,359,444 | A | 10/1994 | Piosenka et al. |
| 5,757,546 | A | 5/1998 | Lipton et al. |
| 5,815,233 | A | 9/1998 | Morokawa et al. |
| 5,861,936 | A | 1/1999 | Sorensen |
| 5,861,940 | A | 1/1999 | Robinson et al. |
| 6,152,563 | A | 11/2000 | Hutchinson et al. |
| 6,243,063 | B1 | 6/2001 | Mayhew et al. |
| 6,491,394 | B1 | 12/2002 | Blum et al. |
| 6,501,443 | B1 | 12/2002 | McMahon |
| 6,517,203 | B1 | 2/2003 | Blum et al. |
| 6,553,504 | B1 | 4/2003 | Katzenelson et al. |
| 6,857,741 | B2 | 2/2005 | Blum et al. |
| 6,986,579 | B2 | 1/2006 | Blum et al. |
| 7,475,984 | B2 | 1/2009 | Blum et al. |
| 7,475,985 | B2 | 1/2009 | Blum et al. |
| 7,497,121 | B2 | 3/2009 | Okuda et al. |
| 7,517,083 | B2 | 4/2009 | Blum et al. |
| 7,600,872 | B2 | 10/2009 | Esser et al. |
| 7,728,949 | B2 | 6/2010 | Clarke et al. |
| 8,052,278 | B2 | 11/2011 | Bovet et al. |
| 8,675,148 | B2 | 3/2014 | Takagi et al. |
| 8,690,321 | B2 | 4/2014 | Lapstun |
| 8,773,629 | B2 | 7/2014 | Uehara et al. |
| 8,896,772 | B2 | 11/2014 | Fraval et al. |
| 8,922,902 | B2 | 12/2014 | Blum et al. |
| 9,052,514 | B2 | 6/2015 | Takama |
| 9,241,669 | B2 | 1/2016 | Pugh et al. |
| 9,304,319 | B2 | 4/2016 | Bar-Zeev et al. |
| 9,541,774 | B2 | 1/2017 | Machida et al. |
| 9,958,703 | B2 | 5/2018 | Pugh et al. |
| 10,036,901 | B2 | 7/2018 | Yadin et al. |
| 10,268,050 | B2 | 4/2019 | To et al. |
| 10,288,904 | B2 | 5/2019 | Yadin et al. |
| 10,466,391 | B2 | 11/2019 | Yadin et al. |
| 2002/0044125 | A1 | 4/2002 | Maltese |
| 2003/0128416 | A1 | 7/2003 | Caracci et al. |
| 2003/0210377 | A1 | 11/2003 | Blum et al. |
| 2003/0231293 | A1 | 12/2003 | Blum et al. |
| 2004/0041745 | A1 | 3/2004 | Chen |
| 2004/0160389 | A1 | 8/2004 | Suyama |
| 2004/0169630 | A1 | 9/2004 | Ide |
| 2005/0146495 | A1 | 7/2005 | MacKinnon et al. |
| 2005/0162367 | A1 | 7/2005 | Kobayashi et al. |
| 2005/0168430 | A1 | 8/2005 | Nishimura et al. |
| 2006/0034003 | A1 | 2/2006 | Zalevsky |
| 2006/0092340 | A1 | 5/2006 | Blum et al. |
| 2006/0126698 | A1 | 6/2006 | Blum et al. |
| 2006/0164593 | A1 | 7/2006 | Peyghambarian et al. |
| 2006/0164687 | A1 | 7/2006 | Huang et al. |
| 2007/0052876 | A1 | 3/2007 | Kaufman et al. |
| 2007/0146873 | A1 | 6/2007 | Ortyn et al. |
| 2007/0236769 | A1 | 10/2007 | Zalevsky |
| 2007/0236800 | A1 | 10/2007 | Cakmakci et al. |
| 2007/0280626 | A1 | 12/2007 | Haddock et al. |
| 2007/0290972 | A1 | 12/2007 | Meredith |
| 2008/0239420 | A1 | 10/2008 | McGrew |
| 2009/0096981 | A1 | 4/2009 | Clarke et al. |
| 2009/0103044 | A1 | 4/2009 | Duston et al. |
| 2009/0237575 | A1 | 9/2009 | Tsi-shi |
| 2009/0279050 | A1 | 11/2009 | McGinn et al. |
| 2010/0007804 | A1 | 1/2010 | Guncer |
| 2010/0026920 | A1 | 2/2010 | Kim et al. |
| 2010/0149444 | A1 | 6/2010 | Hikmet et al. |
| 2010/0157181 | A1 | 6/2010 | Takahashi |
| 2011/0018903 | A1 | 1/2011 | Lapstun et al. |
| 2011/0037837 | A1 | 2/2011 | Chiba et al. |
| 2011/0228181 | A1 | 9/2011 | Jeong et al. |
| 2011/0234934 | A1 | 9/2011 | Chang |
| 2011/0317128 | A1 | 12/2011 | Guilloux et al. |
| 2012/0099040 | A1 | 4/2012 | Robinson et al. |
| 2012/0120333 | A1 | 5/2012 | Chen et al. |
| 2012/0133891 | A1 | 5/2012 | Jiang |
| 2012/0147038 | A1 | 6/2012 | Perez et al. |
| 2012/0194781 | A1 | 8/2012 | Agurok |
| 2012/0212696 | A1 | 8/2012 | Trajikovska et al. |
| 2012/0300171 | A1 | 11/2012 | Gupta et al. |
| 2013/0010256 | A1 | 1/2013 | Haddock et al. |
| 2013/0027655 | A1 | 1/2013 | Blum et al. |
| 2013/0128229 | A1* | 5/2013 | Huang .................. A61B 3/005 |
| | | | 351/239 |
| 2013/0208224 | A1 | 8/2013 | Kizu et al. |
| 2013/0215374 | A1 | 8/2013 | Blum et al. |
| 2013/2008224 | | 8/2013 | Kizu et al. |
| 2013/0250193 | A1 | 9/2013 | Yun et al. |
| 2013/0250223 | A1 | 9/2013 | Takagi et al. |
| 2014/0036172 | A1 | 2/2014 | Trajkovska-Broach et al. |
| 2014/0036183 | A1 | 2/2014 | Asatryan et al. |
| 2014/0118644 | A1 | 5/2014 | Liu et al. |
| 2014/0347405 | A1 | 11/2014 | Kumeta et al. |
| 2015/0116304 | A1 | 4/2015 | Lee et al. |
| 2015/0185503 | A1 | 7/2015 | Tate et al. |
| 2015/0219893 | A1 | 8/2015 | Chen et al. |
| 2015/0378240 | A1 | 12/2015 | Wang et al. |
| 2016/0004128 | A1 | 1/2016 | Wu |
| 2016/0161767 | A1 | 6/2016 | Childers |
| 2016/0209647 | A1* | 7/2016 | Fürsich ............. G02B 27/0075 |
| 2016/0370605 | A1 | 12/2016 | Ain-Kedem |
| 2017/0003519 | A1* | 1/2017 | Burkert .................... G02C 7/06 |
| 2017/0068134 | A1 | 3/2017 | Yadin et al. |
| 2017/0160518 | A1 | 6/2017 | Lanman et al. |
| 2017/0184848 | A1 | 6/2017 | Vallius |
| 2017/0219828 | A1 | 8/2017 | Tsai et al. |
| 2017/0269453 | A1 | 9/2017 | Galstian et al. |
| 2017/0276963 | A1 | 9/2017 | Brennan et al. |
| 2018/0136486 | A1* | 5/2018 | Macnamara .......... G02C 11/10 |
| 2018/0356652 | A1 | 12/2018 | Shibuya et al. |
| 2019/0113772 | A1 | 4/2019 | Yadin et al. |

FOREIGN PATENT DOCUMENTS

| | | |
|---|---|---|
| CN | 108845433 A | 11/2018 |
| EP | 0595705 A1 | 5/1994 |
| EP | 1050775 A1 | 11/2000 |
| EP | 1760515 A2 | 3/2007 |
| EP | 2309310 A1 | 4/2011 |
| EP | 2503787 A1 | 9/2012 |
| EP | 2682810 A1 | 1/2014 |
| JP | S62209412 A | 9/1987 |
| JP | H0289017 A | 3/1990 |

(56) References Cited

FOREIGN PATENT DOCUMENTS

| | | | | |
|---|---|---|---|---|
| JP | H036518 | A | 1/1991 | |
| JP | 2003091013 | A | 3/2003 | |
| JP | 2011203457 | A | 10/2011 | |
| JP | 2012141552 | A | 7/2012 | |
| RU | 2541819 | C2 | 2/2015 | |
| WO | 8102795 | A1 | 10/1981 | |
| WO | 9941639 | A1 | 8/1999 | |
| WO | 03077012 | A2 | 9/2003 | |
| WO | 2008032061 | A2 | 3/2008 | |
| WO | 2011075834 | A1 | 6/2011 | |
| WO | 2012120470 | A1 | 9/2012 | |
| WO | 2014063432 | A1 | 5/2014 | |
| WO | WO-2015186010 | A1 * | 12/2015 | ........... G02B 3/0081 |
| WO | 2017003330 | A1 | 1/2017 | |
| WO | 2017049072 | A1 | 3/2017 | |
| WO | 2017158486 | A1 | 9/2017 | |

OTHER PUBLICATIONS

Lensvector, "Breakthrough Autofocus Technology", 1 page, 2010.
Loktev et al., "Wave front control systems based on modal liquid crystal lenses", Review of Scientific Instruments, vol. 71, No. 9, pp. 3290-3297, Sep. 1, 2000.
Pixeloptics Inc., "The Evolution of Technology—emPower!—The world's First Electronic Focusing Eyewear", 1 page, 2009.
Brunosan., "Headaches in 3D", Saepe cadendo, pp. 1-4, Jan. 29, 2011.
Naumov et al., "Liquid-crystal adaptive lenses with modal control", Optics Letters, vol. 23, No. 13, pp. 992-994, Jul. 1, 1998.
Varioptic SA, "Liquid Lens for Auto Focus (AF)", pp. 1-3, Jul. 31, 2012.
Bagwell et al., "Liquid crystal based active optics", SPIE Proceedings Novel Optical Systems Design and Optimization IX, vol. 6289, pp. 1-12, Sep. 5, 2006.
Holoeye Photonics AG, "LC 2002: Translucent Spatial Light Modulator", pp. 1-2, May 12, 2012.
Varioptic SA, "The Liquid Lens Technology", pp. 1-2, Dec. 2, 2010.
Longtech Optics Co Ltd., "LCD Multiplex Ratio", 1 page, year 2008.
Stiefelhagen et al., "A Model-Based Gaze Tracking System", International Journal of Artificial Intelligence Tools, vol. 6, No. 2, pp. 193-209, year 1997.
Baluja et al., "Non-Intrusive Gaze Tracking Using Artificial Neural Networks", CMU Technical Report, CMU-CS-94-102; pp. 1-14, Jan. 5, 1994.
Jacob, R., "The Use Of Eye Movements In Human-Computer Interaction Techniques: What You Look At Is What You Get", ACM Transactions On Information Systems, vol. 9, No. 3, pp. 152-169, Apr. 1991.
Heinzmann et al., "3-D Facial Pose And Gaze Point Estimation Using A Robust Real-Time Tracking Paradigm", Proceedings of the Third International Conference on Automatic Face and Gesture Recognition, pp. 142-147, Apr. 14-16, 1998.
Wang et al., "Liquid crystal blazed grating beam deflector", Part of the SPIE Conference on Advanced OpticalMemories and Interfaces to Comouter Storage, San Diego, USA, vol. 3468, pp. 43-54, Jul. 1998.
Goodman, "Introduction to Fourier Optics", 3rd edition, published by Roberts & Company, pp. 1-98 year 2005.
Boulder Nonlinear Systems, "Spatial Light Modulators- XY Phase Series", 1 page, 2007.
Boulder Nonlinear Systems, "Spatial Light Modulators—XY Phase Series—draft Specifications", 1 page, 2007.
Holmarc Opto-Mechantronics PVT. Ltd., "Lab Equipment for Research and Manufacturing", pp. 1-24 (relevant p. 18 "Bench Top Rubbing Machine"), Jan. 23, 2015.
Yadin et al., U.S. Appl. No. 16/081,927, filed Sep. 3, 2018.
Yadin et al., U.S. Appl. No. 16/621,698, filed Dec. 12, 2019.
EP Application # 18869416 Search Report dated Jun. 16, 2021.
International Application # PCT/IB2020/054524 Search Report dated Aug. 31, 2020.
U.S. Appl. No. 16/085,581 Office Action dated Nov. 3, 2020.
EP Application # 20199016.5 Search Report dated Nov. 30, 2020.
U.S. Appl. No. 16/085,581 Office Action dated Sep. 20, 2021.
EP Application # 21202537.3 Search Report dated Nov. 4, 2021.
CA Application # 2,947,809 Office Action dated Apr. 19, 2021.
CA Application # 2,939,664 Office Action dated Apr. 20, 2021.
U.S. Appl. No. 16/085,581 Office Action dated May 7, 2021.
U.S. Appl. No. 16/566,910 Office Action dated Jun. 24, 2021.
International Application # PCT/IB2018/057841 search report dated Jan. 15, 2019.
EP Application # 19841482.3 Search Report dated May 13, 2022.
International Application # PCT/IB2022/052812 Search Report dated Jun. 30, 2022.

\* cited by examiner

SPECTACLES WITH ELECTRICALLY-TUNABLE LENSES CONTROLLABLE BY AN EXTERNAL SYSTEM

RELATED APPLICATION INFORMATION

The present application claims priority from U.S. Provisional Patent Application Ser. No. 62/572,585 of Yadin, et al., filed Oct. 16, 2017, the disclosure of which is hereby incorporated herein by reference.

FIELD OF THE INVENTION

The present invention relates generally to optical devices, and particularly to electrically-tunable lenses.

BACKGROUND OF THE INVENTION

Tunable lenses are optical elements whose optical characteristics, such as the focal length and/or the location of the optical center, can be adjusted during use, typically under electronic control. Such lenses may be used in a wide variety of applications. For example, U.S. Pat. No. 7,475,985 describes the use of an electro-active lens for the purpose of vision correction.

Electrically-tunable lenses typically contain a thin layer of a suitable electro-optical material, i.e., a material whose local effective index of refraction changes as a function of the voltage applied across the material. An electrode or array of electrodes is used to apply the desired voltages in order to locally adjust the refractive index to the desired value. Liquid crystals are the electro-optical material that is most commonly used for this purpose (wherein the applied voltage rotates the molecules, which changes the axis of birefringence and thus changes the effective refractive index), but other materials, such as polymer gels, with similar electro-optical properties can alternatively be used for this purpose.

Some tunable lens designs use an electrode array to define a grid of pixels in the liquid crystal, similar to the sort of pixel grid used in liquid-crystal displays. The refractive indices of the individual pixels may be electrically controlled to give a desired phase modulation profile. (The term "phase modulation profile" is used in the present description and in the claims to mean the distribution of the local phase shifts that are applied to light passing through the layer as the result of the locally-variable effective refractive index over the area of the electro-optical layer of the tunable lens.) Lenses using grid arrays of this sort are described, for example, in the above-mentioned U.S. Pat. No. 7,475,985.

PCT International Publication WO 2014/049577, whose disclosure is incorporated herein by reference, describes an optical device comprising an electro-optical layer, having an effective local index of refraction at any given location within an active area of the electro-optical layer that is determined by a voltage waveform applied across the electro-optical layer at the location. An array of excitation electrodes, including parallel conductive stripes extending over the active area, is disposed over one or both sides of the electro-optical layer. Control circuitry applies respective control voltage waveforms to the excitation electrodes and is configured to concurrently modify the respective control voltage waveforms applied to excitation electrodes so as to generate a specified phase modulation profile in the electro-optical layer.

U.S. Patent Application Publication 2012/0133891 describes an electro-optical apparatus and method for correcting myopia that includes at least one adaptive lens, a power source, and an eye tracker. The eye tracker includes an image sensor and a processor operatively connected to the adaptive lens and the image sensor. The processor is configured to receive electrical signals from the image sensor and to control the correction power of the adaptive lens to correct myopia, with the correction power dependent on a user's gaze distance and myopia prescription strength.

SUMMARY

There is provided in accordance with an embodiment of the present disclosure, a system for controlling at least one focus aspect of adaptive spectacles having at least one electrically-tunable lens, the system including a housing, which is physically separate from the adaptive spectacles, a display screen mounted in the housing and configured to be viewed through the adaptive spectacles by a person, a sensor mounted in the housing and configured to detect a relative position of the adaptive spectacles with respect to the display screen, an interface configured to communicate with the adaptive spectacles, and a controller configured to receive an input signal from the sensor, the input signal being indicative of the relative position of the adaptive spectacles with respect to the display screen, and output, in response to the input signal, a command signal for sending to the adaptive spectacles via the interface to adjust the at least one focus aspect of the at least one electrically-tunable lens.

Further in accordance with an embodiment of the present disclosure, the command signal is indicative of at least one refractive power to which the at least one electrically-tunable lens will be adjusted.

Still further in accordance with an embodiment of the present disclosure, the controller is configured to calculate, based on the relative position, the at least one refractive power to which the at least one electrically-tunable lens will be adjusted.

Additionally, in accordance with an embodiment of the present disclosure, the controller is configured to calculate the at least one refractive power, based on the relative position and a given visual accommodation capability of the person wearing the adaptive spectacles.

Moreover, in accordance with an embodiment of the present disclosure, the system includes the adaptive spectacles, the adaptive spectacles being configured to receive the command signal and adjust the at least one electrically-tunable lens to provide the at least one refractive power.

Further in accordance with an embodiment of the present disclosure, the command signal is indicative of an optical center of the at least one electrically-tunable lens to which the at least one electrically-tunable lens is to be adjusted in order to align a line-of-sight of the person wearing the adaptive spectacles and viewing the display screen with the optical center of the at least one electrically-tunable lens.

Still further in accordance with an embodiment of the present disclosure, the controller is configured to calculate the optical center of the at least one electrically-tunable lens based on the relative position so that the line-of-sight of the person wearing the adaptive spectacles and viewing the display screen is aligned with the optical center of the at least one electrically-tunable lens when the at least one electrically-tunable lens will be adjusted.

Additionally, in accordance with an embodiment of the present disclosure, the system includes the adaptive spectacles, the adaptive spectacles being configured to receive the command signal and adjust the optical center of the at least one electrically-tunable lens to align the line-of-sight of the person wearing the adaptive spectacles and viewing the display screen with the optical center of the at least one electrically-tunable lens.

Moreover, in accordance with an embodiment of the present disclosure, the interface, the controller, the sensor, and the display screen are implemented in a mobile device.

Further in accordance with an embodiment of the present disclosure, the sensor includes a front-facing camera disposed adjacent to the display screen, and the controller is configured to determine the relative position of the adaptive spectacles with respect to the display screen based on image analysis of images captured by the front-facing camera of the mobile device.

Still further in accordance with an embodiment of the present disclosure, the sensor includes a depth-sensor.

Additionally in accordance with an embodiment of the present disclosure, the controller is configured to determine when the person wearing the adaptive spectacles is viewing or using the display screen, and in response to determining that the person wearing the adaptive spectacles is viewing or using the display screen determine the relative position, and prepare the command signal, based on the relative position, for sending to the adaptive spectacles to adjust the at least one focus aspect of the at least one electrically-tunable lens.

Moreover, in accordance with an embodiment of the present disclosure, the controller is configured to determine when the person wearing the adaptive spectacles is viewing the display screen based on analyzing an eye gaze direction of the person captured by the sensor.

Further in accordance with an embodiment of the present disclosure, the sensor is implemented as part of a vehicle gaze detection system and the display screen is implemented as part of a vehicle instrument panel.

Still further in accordance with an embodiment of the present disclosure, the controller is configured to determine when the person wearing the adaptive spectacles is using the display screen based on user interaction with a touch sensitive portion of the display screen.

Additionally, in accordance with an embodiment of the present disclosure, the interface is configured to receive an orientation reading from the adaptive spectacles, and the controller is configured to correct the relative position based on the orientation reading.

Moreover in accordance with an embodiment of the present disclosure, the system includes a processor configured to execute an eye therapy software application to display a plurality of images on the display screen, the plurality of images being generated to challenge a visual accommodation capability of the person, wherein the controller is configured to calculate at least one refractive power to which the at least one electrically-tunable lens will be adjusted based on the relative position and a given visual accommodation capability to which the person is to be challenged, and prepare the command signal to include the at least one refractive power to which the at least one electrically-tunable lens will be adjusted.

There is also provided in accordance with still another embodiment of the present disclosure, a system for controlling adaptive spectacles, the system including a mobile device including a housing, which is physically separate from the adaptive spectacles, a display screen mounted in the housing and configured to be viewed through the adaptive spectacles by a person, a sensor mounted in the housing and configured to detect a relative position of the adaptive spectacles with respect to the display screen, a first interface configured to communicate with the adaptive spectacles, and a controller configured to receive an input signal from a sensor, the input signal being indicative of the relative position of the adaptive spectacles with respect to the display screen, and output in response to the input signal, a command signal for sending to the adaptive spectacles via the first interface, and the adaptive spectacles including a spectacle frame, at least one electrically-tunable lens mounted in the spectacle frame, a second interface configured to receive the command signal from the device, and control circuitry configured to adjust the at least one focus aspect of the at least one electrically-tunable lens based on the command signal.

Further in accordance with an embodiment of the present disclosure, the command signal includes at least one refractive power to which the at least one electrically-tunable lens will be adjusted.

Still further in accordance with an embodiment of the present disclosure, the control circuitry is configured to calculate, based on the relative position, at least one refractive power to which the at least one electrically-tunable lens will be adjusted.

Additionally, in accordance with an embodiment of the present disclosure, the control circuitry is configured to calculate the at least one refractive power, based on the relative position and a given visual accommodation capability of the person.

Moreover, in accordance with an embodiment of the present disclosure, the control circuitry is configured to adjust the at least one electrically-tunable lens to provide the at least one refractive power.

Further in accordance with an embodiment of the present disclosure, the command signal includes an indication of an optical center of the at least one electrically-tunable lens to which the at least one electrically-tunable lens is to be adjusted in order to align a line-of-sight of the person wearing the adaptive spectacles and viewing the display screen with the optical center of the at least one electrically-tunable lens.

Moreover, in accordance with an embodiment of the present disclosure, the control circuitry is configured to calculate an optical center of the at least one electrically-tunable lens based on the relative position so that a line-of-sight of the person wearing the adaptive spectacles and viewing the display screen is aligned with the optical center of the at least one electrically-tunable lens when the at least one electrically-tunable lens will be adjusted.

Still further in accordance with an embodiment of the present disclosure, the control circuitry is configured to adjust the optical center of the at least one electrically-tunable lens to align the line-of-sight of the person wearing the adaptive spectacles and viewing the display screen with the optical center of the at least one electrically-tunable lens.

Additionally, in accordance with an embodiment of the present disclosure, the first interface is configured to receive an orientation reading from the adaptive spectacles, and the controller is configured to correct the relative position based on the orientation reading.

There is also provided in accordance with still another embodiment of the present disclosure, a system for managing eye therapy via at least one focus aspect of adaptive spectacles having at least one electrically-tunable lens, the system including an interface configured to communicate with the adaptive spectacles, a processor configured to execute an eye therapy software application to display a plurality of images on a display screen, the plurality of images being generated to challenge a visual accommodation capability of the person, and a controller configured to calculate at least one refractive power to which the at least one electrically-tunable lens will be adjusted at least based on a given visual accommodation capability to which the person is to be challenged, and output, to the adaptive spectacles via the interface, a command signal including the at least one refractive power to which the at least one electrically-tunable lens will be adjusted.

There is also provided in accordance with still another embodiment of the present disclosure, a method for controlling at least one focus aspect of adaptive spectacles having at least one electrically-tunable lens, the method including detecting, using a sensor, a relative position of the adaptive spectacles with respect to a display screen configured to be viewed through the adaptive spectacles by a person, the display screen being mounted in a housing with the sensor, the housing being physically separate from the adaptive spectacles, communicating with the adaptive spectacles, receiving an input signal from the sensor indicative of the relative position of the adaptive spectacles with respect to the display screen, and outputting, in response to the input signal, a command signal for sending to the adaptive spectacles to adjust the at least one focus aspect of the at least one electrically-tunable lens.

Moreover, in accordance with an embodiment of the present disclosure, the command signal is indicative of at least one refractive power to which the at least one electrically-tunable lens will be adjusted.

Further in accordance with an embodiment of the present disclosure, the method includes calculating, based on the relative position, at least one refractive power to which the at least one electrically-tunable lens will be adjusted.

Still further in accordance with an embodiment of the present disclosure, the method includes calculating at least one refractive power, based on the relative position and a given visual accommodation capability of the person wearing the adaptive spectacles.

Additionally, in accordance with an embodiment of the present disclosure, the command signal is indicative of an optical center of the at least one electrically-tunable lens to which the at least one electrically-tunable lens is to be adjusted in order to align a line-of-sight of the person wearing the adaptive spectacles and viewing the display screen with the optical center of the at least one electrically-tunable lens.

Moreover, in accordance with an embodiment of the present disclosure, the method includes calculating an optical center of the at least one electrically-tunable lens based on the relative position so that a line-of-sight of the person wearing the adaptive spectacles and viewing the display screen is aligned with the optical center of the at least one electrically-tunable lens when the at least one electrically-tunable lens will be adjusted.

Further in accordance with an embodiment of the present disclosure, the method includes determining the relative position of the adaptive spectacles with respect to the display screen based on image analysis of images captured.

Still further in accordance with an embodiment of the present disclosure, the method includes determining when the person wearing the adaptive spectacles is viewing or using the display screen, and in response to determining that the person wearing the adaptive spectacles is viewing or using the display screen determining the relative position, and preparing the command signal, based on the relative position, for sending to the adaptive spectacles to adjust the at least one focus aspect of the at least one electrically-tunable lens.

Additionally, in accordance with an embodiment of the present disclosure, the method includes determining when the person wearing the adaptive spectacles is viewing the display screen based on analyzing an eye gaze direction of the person captured by the sensor.

Moreover, in accordance with an embodiment of the present disclosure, the method includes determining when the person wearing the adaptive spectacles is using the display screen based on user interaction with a touch sensitive portion of the display screen.

Further in accordance with an embodiment of the present disclosure, the method includes executing an eye therapy software application to display a plurality of images on the display screen, the plurality of images being generated to challenge a visual accommodation capability of the person, calculating at least one refractive power to which the at least one electrically-tunable lens will be adjusted based on the relative position and a given visual accommodation capability to which the person is to be challenged, and preparing the command signal to include the at least one refractive power to which the at least one electrically-tunable lens will be adjusted.

There is also provided in accordance with still another embodiment of the present disclosure, a method for controlling adaptive spectacles, the method including performing in a mobile device including a housing which houses a sensor and a display screen detecting, using the sensor, a relative position of the adaptive spectacles with respect to the display screen configured to be viewed through the adaptive spectacles by a person, the housing being physically separate from the adaptive spectacles, communicating with the adaptive spectacles, receiving an input signal indicative of the relative position of the adaptive spectacles with respect to the display screen, and outputting, in response to the input signal, a command signal for sending to the adaptive spectacles to adjust the at least one focus aspect of the at least one electrically-tunable lens, and the adaptive spectacles adjusting the at least one focus aspect of at least one electrically-tunable lens of the adaptive spectacles based on the command signal.

Still further in accordance with an embodiment of the present disclosure, the command signal includes at least one refractive power to which the at least one electrically-tunable lens will be adjusted.

Additionally, in accordance with an embodiment of the present disclosure, the method includes calculating, based on the relative position, at least one refractive power to which the at least one electrically-tunable lens will be adjusted.

Moreover, in accordance with an embodiment of the present disclosure, the method includes calculating at least one refractive power, based on the relative position and a given visual accommodation capability of the person.

Further in accordance with an embodiment of the present disclosure, the method includes adjusting the at least one electrically-tunable lens to provide the at least one refractive power.

Still further in accordance with an embodiment of the present disclosure, the command signal includes an indication of an optical center of the at least one electrically-tunable lens to which the at least one electrically-tunable lens is to be adjusted in order to align a line-of-sight of the person wearing the adaptive spectacles and viewing the display screen with the optical center of the at least one electrically-tunable lens.

Additionally, in accordance with an embodiment of the present disclosure, the method includes calculating an optical center of the at least one electrically-tunable lens based on the relative position so that a line-of-sight of the person wearing the adaptive spectacles and viewing the display screen is aligned with the optical center of the at least one electrically-tunable lens when the at least one electrically-tunable lens will be adjusted.

Moreover, in accordance with an embodiment of the present disclosure, the method includes adjusting the optical center of the at least one electrically-tunable lens to align the line-of-sight of the person wearing the adaptive spectacles and viewing the display screen with the optical center of the at least one electrically-tunable lens.

There is also provided in accordance with still another embodiment of the present disclosure, a method for managing eye therapy via at least one focus aspect of adaptive spectacles having at least one electrically-tunable lens, the method including communicating with the adaptive spectacles, executing an eye therapy software application to display a plurality of images on a display screen, the plurality of images being generated to challenge a visual accommodation capability of the person, calculating at least one refractive power to which the at least one electrically-tunable lens will be adjusted at least based on a given visual accommodation capability to which the person is to be challenged, and outputting, to the adaptive spectacles via the interface, a command signal including the at least one refractive power to which the at least one electrically-tunable lens will be adjusted.

There is also provided in accordance with still another embodiment of the present disclosure, a software product, including a non-transient computer-readable medium in which program instructions are stored, which instructions, when read by a central processing unit (CPU), cause the CPU to receive an input signal from a sensor, the input signal being indicative of a relative position of adaptive spectacles with respect to a display screen, which is configured to be viewed through the adaptive spectacles by a person, the display screen being mounted in a housing with the sensor, the housing being physically separate from the adaptive spectacles, and output, in response to the input signal, a command signal for sending to the adaptive spectacles to adjust the at least one focus aspect of the at least one electrically-tunable lens.

There is also provided in accordance with still another embodiment of the present disclosure, a software product, including a non-transient computer-readable medium in which program instructions are stored, which instructions, when read by a central processing unit (CPU), cause the CPU to communicate with adaptive spectacles having at least one electrically-tunable lens, execute an eye therapy software application to display a plurality of images on a display screen, the plurality of images being generated to challenge a visual accommodation capability of the person, calculate at least one refractive power to which the at least one electrically-tunable lens will be adjusted at least based on a given visual accommodation capability to which the person is to be challenged, and output, to the adaptive spectacles via the interface, a command signal including the at least one refractive power to which the at least one electrically-tunable lens will be adjusted.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Embodiments of the present invention provide an automatic vision correction system comprising two sub-systems. One sub-system includes adaptive spectacles with electrically-tunable lenses (such as the ones described in PCT International Publication WO 2015/186010, whose disclosure is incorporated herein by reference) with a capability to connect to an external sub-system, and receive commands from that external sub-system to change the focal distance and/or optical center (also known as optical axis) of its tunable lenses and/or receive information that can be used by the adaptive spectacles to determine the needed focus change and/or an adjustment to the optical center. It should be noted that the optical center of one or more of the electrically-tunable lenses may be adjusted to accommodate an angle of view determined by the external sub-system. For example, the optical quality of a liquid crystal (LC) tunable lenses is optimal at the center of the lens, and degrades with the distance from the center. Since the LC lens is positioned at a distance from a person's eye, when the person rotates his/her eye to view different directions, the line-of-sight crosses the LC lens at different locations. By shifting the optical center of the tunable lens in accordance with the angle of view, thereby centering the LC lens with the line-of-sight, the lens quality can be improved, particularly when the user is looking through an area near the edge of the lens and/or when a lens with a narrow field of view is being used to implement the electrically-tunable lenses. Shifting optical centers of adaptive spectacles in a different setting is described in PCT International Publication WO 2017/182906, whose disclosure is incorporated herein by reference.

The second, "external" sub-system can be one of many types of computing-capable systems with a capability to connect to the adaptive spectacles and submit commands and/or information as described above. The external sub-system may be capable of determining the context of the use of the adaptive spectacles (for example, assess the relative position of the adaptive spectacles with respect to a display screen being viewed by the person wearing the adaptive spectacles in order to calculate the focus change and/or the adjustment to the optical center) or it may apply any desired policy to control the glasses (for example, execute a predetermined set of focus-change commands as part of an accommodation training eye-therapy session). The term "relative position", as used in the claims and the specification, is defined to include an angular orientation of the adaptive spectacles with respect to the display screen and/or at least one distance between the adaptive spectacles and the display screen.

Communication between the two sub-systems may be established using existing variety of standard and proprietary protocols. These may be wireless protocols, such as Bluetooth® or WiFi®, or wired protocols such as Universal Serial Bus (USB), or low-level serial protocols like Inter-integrated Circuit (I²C) or SPA. A higher-level-protocol providing a predefined set of commands and messages may be used between the two sub-systems to perform the interaction. That protocol may vary depending on the application and the identity of the external sub-system. Examples of such systems follow.

People with presbyopia have difficulty focusing to close distances, and in particular hand-held device distance, such as a mobile phone, which can be in the range of 25 cm-50 cm (+2 diopters to +4 diopters). One embodiment of the present invention provides a system that comprises a hand-held mobile device such as a mobile phone, a tablet, a smart watch, or an e-reader with a capability to determine the relative position of the adaptive spectacles with respect to the display screen of the mobile device. Such capability may be realized in various ways such as a dedicated depth-sensor (such as the depth sensor of Apple's iPhone® X), a front facing camera (camera located on the display side—either using single or multiple aperture to determine depth) with accompanying image-processing running on the device, and possibly other depth sensing components and techniques. The hand-held mobile device can determine that the user is currently using it, continuously assess the relative position of the adaptive spectacles with respect to the display screen, and communicate this information to the adaptive spectacles, or even command the adaptive spectacles to change focus and/or optical center(s) as needed.

For example, a user may have a limited accommodation ability of 1 diopter. When the user holds the device at a distance of 33 cm (3 diopters), the device will identify this distance, conclude that the user requires +2 diopter vision correction to that distance, and command the lenses mounted on the adaptive spectacles to switch to a power of +2 diopter via the control channel (e.g. Bluetooth®).

The above description, as well as some of the examples described herein below, describe helping people with presbyopia to view a close object in focus. Substantially the same systems and methods may also be implemented to provide myopia control and for relieving eye strain for people that do not suffer from presbyopia. In these cases, the adaptive spectacles reduce the amount of accommodation required by the person even though the person is capable of greater accommodation. Additionally, the systems and methods described herein may be implemented for eye testing to determine a prescription for vision correction. For example, optometrists may use a screen in the examination room (typically installed on a wall at least 3 meters away from the patient) while the patient is wearing adaptable spectacles. The patient, or optometrist, controls the optical power applied to the tunable lenses, and the optical center of the tunable lenses is automatically controlled so that the center of the tunable lenses is aligned with the line-of-sight between the patient and the screen. Similar tests can be conducted for determining a prescription for presbyopia with the patient (or optometrist) holding a mobile device 30-40 cm away from the patient's eyes while tuning the refractive power of the spectacles, and controlling the optical center of the tunable lens to be aligned automatically with the line-of-sight between the patient and the screen of the mobile device.

Laptop and desktop computers may utilize more powerful distance detection equipment such as a desktop eye tracker or desktop depth sensor (such as Microsoft's Kinect®) in order to correct for presbyopia. While the above applications are described to help people with presbyopia, it can be easily modified to handle eye-relief (performing partial or full refractive correction to reduce the need for human accommodation) or an eye therapy application described in more detail below.

Some people suffer from limited accommodation capability and can benefit from special therapy. Such therapy includes training sessions forcing the patient to accommodate—for example, by displaying a stereoscopic three-dimensional (3D) image on a 3D computer screen. These treatments also make use of refractive lenses aiming to shift the focal distance and challenge the patient's accommodation system. These treatments use continuous changes of the stimuli so as to trigger the patient's eyes to change their accommodation continuously for a certain amount of time, resulting in improvement of the accommodation capability. Such a system can be realized using the adaptive spectacles having electrically-tunable lenses in conjunction with a PC, mobile phone, or other computing platform running the session and controlling the adaptive spectacles either wirelessly or via a tethered connection. Eye therapy may also be implemented using a Virtual Reality (VR) headset, displaying the images at varying virtual distances, to trigger different accommodation reflex reactions, and controlling the adaptive spectacles (installed inside the VR headset) to change focus according to the treatment plan.

When driving, people have to continually change their vision focus from far distances, when looking at the road, to close distance when looking at the vehicle instrument panel (e.g., car gauges and other displays). For people with presbyopia, this is a difficult task and vision quality is poor. Embodiments of the present invention include installing a driver gaze detection system in the car (examples of such systems can be found in existing car and truck models—designed to detect and alert for driver fatigue or distraction). The gaze detection system may determine the relative position of the adaptive spectacles with respect to the vehicle instrument panel and communicate it, or focus and/or optical center information, to the adaptive spectacles. which then correct the driver's vision as needed.

When driving, for safety reasons, it may be beneficial to make sure a significant part of the lens, typically the top part, will constantly stay focused to far distance. In such cases, when the system identifies that the user requires vision correction for close distances, the positive lenses can be realized on only a part of the lens panel, for example using techniques described in the above PCT International Publication WO 2015/186010.

It should be noted that documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

System Description

Figure 1A:
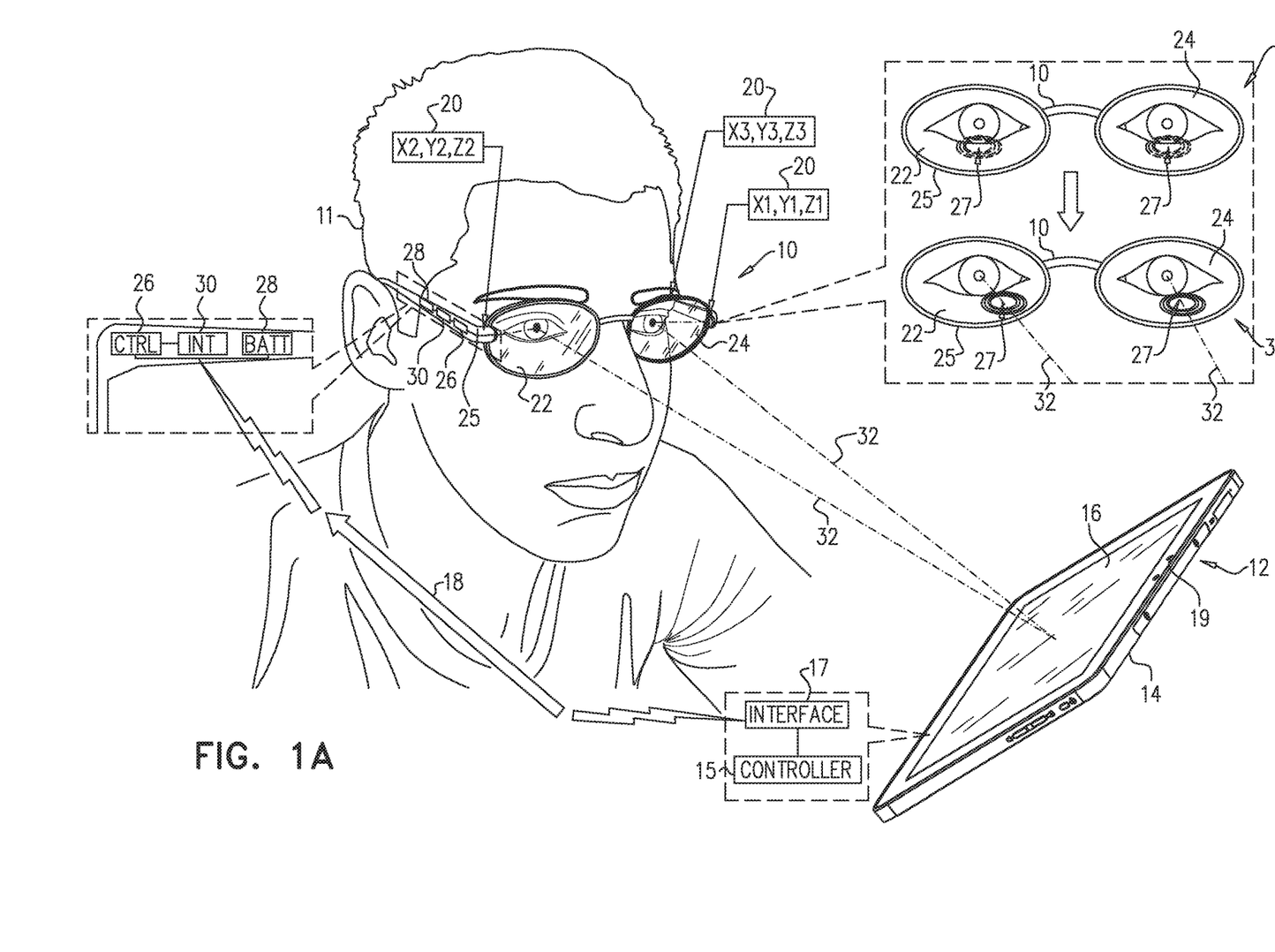
FIG. 1A is a schematic, pictorial illustration of adaptive spectacles being worn by a person using a mobile device, constructed and operative in accordance with an embodiment of the present invention.

Reference is now made to FIG. 1A, which is a schematic, pictorial illustration of adaptive spectacles 10 being worn by a person 11 using a mobile device 12, constructed and operative in accordance with an embodiment of the present invention.

The mobile device 12 includes a housing 14, which is physically separate from the adaptive spectacles 10. The mobile device 12 also includes, mounted in the housing 14, a controller 15, a display screen 16, an interface, and a sensor 19. The display screen 16 is configured to be viewed through the adaptive spectacles 10 by the person 11. The interface 17 is configured to communicate with the adaptive spectacles 10 via a wired and/or wireless link 18. The sensor 19, possibly in conjunction with the controller 15, is configured to detect a relative position 20 of the adaptive spectacles 10 with respect to the display screen 16. The relative position may include an angular orientation of the adaptive spectacles 10 with respect to the display screen 16 and/or at least one distance between the adaptive spectacles 10 and the display screen 16. The relative position may include detecting several predefined points on the adaptive spectacles 10 and/or detecting the adaptive spectacles 10 using machine learning techniques, by way of example only. The mobile device 12 is described in more detail below after the adaptive spectacles 10 are now described briefly.

Adaptive spectacles 10 comprise electrically-tunable lenses 22 and 24, mounted in a spectacle frame 25. The optical properties of the electrically-tunable lenses 22 and 24, including focal length and an optical center 27 are controlled by control circuitry 26, powered by a battery 28 or other power source. Control circuitry 26 typically comprises an embedded microprocessor with hard-wired and/or programmable logic components and suitable interfaces for carrying out the functions that are described herein. The adaptive spectacles 10 also include an interface 30 for communicating with an external system, such as the mobile device 12. These and other elements of adaptive spectacles 10 are typically mounted on, or in, spectacle frame 25, or may alternatively be contained in a separate unit (not shown) connected by wire to spectacle frame 25.

The mobile device 12 is now described in more detail. The sensor 19 may include a front-facing camera (camera located on the display side of the mobile device 12) disposed adjacent to the display screen 16. The sensor 19 may either use a single or multiple aperture to determine depth (e.g., the distance between the adaptive spectacles 10 and the display screen 16) with accompanying image-processing running on the controller 15, and possibly other depth sensing components and techniques. In some embodiments, the sensor 19 may include a depth-sensor such as the depth sensor of Apple's iPhone® X. Other sensors such as accelerometers and gyroscopes disposed in the mobile device 12 and/or in the adaptive spectacles 10 may also provide information regarding the relative position. The accelerometers and gyroscopes may be implemented as part of an inertial measurement unit (IMU). In some embodiments, the interface 17 of the mobile device 12 is configured to receive an orientation reading (e.g., captured by an IMU of the adaptive spectacles 10) from the adaptive spectacles 10 and the controller 15 is configured to correct the relative position based on the orientation reading. For example, some orientations of the adaptive spectacles 10 may be difficult to detect from the data captured by the sensor 19. For these orientations, the orientations readings captured by sensor(s) of the adaptive spectacles 10 may be used by the controller 15 to correct the relative position.

The controller 15 is configured to receive an input signal from the sensor 19. The input signal is indicative of the relative position of the adaptive spectacles 10 with respect to the display screen 16. The controller 15 may be configured to determine the relative position of the adaptive spectacles 10 with respect to the display screen 16 based on image analysis of images captured by the sensor 19 (e.g., the front-facing camera) of the mobile device 12. The relative position may include a distance from the display screen 16 to the adaptive spectacles 10 and/or an angular orientation of adaptive spectacles 10 with respect to the display screen 16 based on an appropriate coordinate system.

FIG. 1A shows three relative locations (X1,Y1,Z1 and X2,Y2,Z2 and X3,Y3,Z3) detected by the sensor 19. The three relative locations shown in FIG. 1A locate the sides of the adaptive spectacles 10 (X1,Y1,Z1 and X2,Y2,Z2) as well as an upper point (X3,Y3,Z3) of the adaptive spectacles 10 with respect to the display screen 16. Appropriate selection of three relative locations is generally sufficient to identify an angular orientation of the adaptive spectacles 10 with respect to the display screen 16 and at least one distance between the adaptive spectacles 10 and the display screen 16. Different points on the adaptive spectacles 10 may be similarly identified to identify the angular orientation of the adaptive spectacles 10 with respect to the display screen 16 and the distance(s) between the adaptive spectacles 10 and the display screen 16. Although the example of FIG. 1A uses a Cartesian Coordinate system, any suitable coordinate system may be used. Using more than three locations may improve accuracy of the resulting calculation(s).

The distance between the display screen 16 and the adaptive spectacles 10 is generally sufficient to determine a focus adjustment to the electrically-tunable lenses 22 and 24. The angular orientation (based on the relative location of three or more points) of the adaptive spectacles 10 with respect to the display screen 16 is generally also needed in order to determine an adjustment to the optical center(s) 27 of the electrically-tunable lenses 22 and 24 as will be described in more detail below. In some embodiments, the orientation of the adaptive spectacles 10 and the distance between the adaptive spectacles 10 and the display screen may be inferred from eye and/or head position.

The controller 15 may be configured to calculate, based on the relative position (e.g., distance from the display screen 16 to the adaptive spectacles 10) and a given visual accommodation capability of the person wearing the adaptive spectacles 10, at least one refractive power to which the electrically-tunable lenses 22 and 24 will be adjusted. It should be noted that only one, or both, of the electrically-tunable lenses 22 and 24 may be adjusted. If both of the electrically-tunable lenses 22 and 24 are to be adjusted, then each of the electrically-tunable lenses 22 and 24 will be adjusted to the same refractive power or different refractive powers. In some embodiments the at least one refractive power is calculated by the adaptive spectacles 10 as described below in more detail.

The following example illustrates how the refractive power of the electrically-tunable lenses 22 and 24 may be calculated. For a person with a limited accommodation of 1 diopter, the nearest point that can be seen clearly would be 1 m (100 cm) from the person's eyes. To see an object placed at 25 cm from the person's eyes would entail adjusting the refractive power of the electrically-tunable lenses 22 and 24 based on the lens formula (or based on diopter calculations):

1/focal length (f)=1/object distance (u)+1/image distance (v). Since the image formed is a virtual image, a minus sign is assigned to the image distance so the formula may be rewritten as 1/f=1/u−1/v. Substituting for the object distance of 25 cm and the image distance of 100 cm, 1/f=1/25−1/100. Hence f=100/3=33.3 cm which is equivalent of 100/33.3=3 diopters. The above calculation could be performed for each of the electrically-tunable lenses 22 and 24 separately resulting in a different correction for each of the electrically-tunable lenses 22 and 24.

The controller 15 is configured to generate a command signal that is indicative of the calculated refractive power(s) to which the electrically-tunable lens(es) 22, 24 will be adjusted. The given visual accommodation capability of the person wearing the adaptive spectacles 10 may be received by the mobile device 12 from the spectacles 10 in a set up stage or determined by the mobile device 12 in a configuration stage, for example, by asking the person 11 to hold the device and adjust the adaptive spectacles 10 until the person 11 indicates an image shown on the display screen 16 is being clearly seen by the person 11.

Alternatively, the given accommodation capability of the person wearing the adaptive spectacles 10 may be stored by the adaptive spectacles 10, which receives a signal indicative of the total required accommodation from the mobile device 12. The spectacles 10 then calculates the refractive power(s) to which the electrically-tunable lens(es) 22, 24 will be adjusted based on the given accommodation capability and the total required accommodation of the received signal.

Additionally, or alternatively, the controller 15 may be configured to calculate the optical center(s) 27 of the electrically-tunable lens(es) 22, 24 based on the relative position of the adaptive spectacles 10 with respect to the display screen 16 so that a line-of-sight 32 of the person 11 wearing the adaptive spectacles 10 and viewing the display screen 16 is aligned with the optical center(s) 27 of the electrically-tunable lens(es) 22, 24 when the electrically-tunable lens(es) 22, 24 will be adjusted. The controller 15 is configured to generate the command signal to be indicative of the optical center(s) 27 of the electrically-tunable lens(es) 22, 24 to which the electrically-tunable lens(es) 22, 24 are to be adjusted in order to align the line-of-sight 32 of the person 11 wearing the adaptive spectacles 10 with the optical center(s) 27 of the electrically-tunable lens(es) 22, 24. FIG. 1A shows a first position 29 of the optical centers 27 of the electrically-tunable lenses 22 and 24 and a shifted, second position 31, of the optical centers 27 calculated based on the person 11 looking sideways at the display screen 16.

One method for calculating the optical center(s) 27 may be based on the normal vertex distance and the location of the center of rotation of the eye, as will now be explained. When the eye rotates in its orbit, there is a point within the eyeball that is more or less fixed relative to the orbit. This is the center of rotation of the eye. It may be considered, for convenience, that the center of rotation of the eye lies on the line-of-sight of the eye 13.5 mm behind the anterior pole of the cornea when the eye is in the straight-ahead position, that is when the line-of-sight is perpendicular to both the base line and the frontal plane. The vertex distance may be assumed to be 12 mm, which provides a total distance from the center of eye rotation to the back surface of the spectacle lens to be 25.5 mm. Geometric calculations may then be used, based on the relative position of the adaptive spectacles 10 with respect to the display screen 16 to calculate the optical center(s) 27. The vertical and horizontal positions of the pupils captured in an image in a calibration stage may be used to provide X and Y positions (in the X-Y plane parallel to the plane of the electrically-tunable lenses 22 and 24) of the centers of rotation of the eyes. One way of executing such a calibration is by capturing an image of the person wearing the spectacles while the person is looking straight ahead. Another way of executing the calibration is by capturing an image of the person wearing the adaptive spectacles 10 even while looking to the side and/or up or down. The spectacle frame 25 and the pupils of the person are identified in the captured image, and the coordinates of the center of rotation of each eye may then be calculated using geometric calculation, based on the location of the pupils in the image relative to the spectacle frame 25, the dimensions of the spectacle frame 25, and the estimation of the distance between the electrically-tunable lenses 22 and 24 and the center of rotation (e.g. 25.5 mm). The vertex distance may vary from spectacle to spectacle, but can generally be measured for any pair of adaptive spectacles 10. The distance from the center of rotation of the eye to the anterior pole of the cornea may also vary between people. This distance may also be determined for the person 11 and used in the calculations or the assumed distance of 13.5 mm may be used instead.

In some embodiments, the controller 15 does not determine the refractive power and/or the optical center(s) 27, but includes the relative position in the command signal for the adaptive spectacles 10 to determine the refractive power and/or the optical center(s) 27 based on the relative position. The command signal may be indicative of the relative position, for example, based on an image captured by the sensor 19.

The controller 15 is configured to output, in response to the input signal, the command signal for sending to the adaptive spectacles 10, via the interface 17, for the adaptive spectacles 10 to adjust the focus aspect(s) of the electrically-tunable lens 22, 24.

In some embodiments, the controller 15 is configured to calculate the relative position periodically when it is estimated or determined that the person 11 wearing the adaptive spectacles 10 is using or viewing the display screen. The controller 15 may be configured to determine when the person 11 wearing the adaptive spectacles 10 is viewing the display screen 16 (e.g., based on eye gaze tracking), and/or using the display screen 16 (based on user interaction with a touch sensitive portion of the display screen 16), and/or identifying movements of the mobile device 12 typically associated with using the display screen 16 such as movement in which the mobile device 12 is placed with the screen facing up using an inertial measurement unit, by way of example only. In response to determining that the person 11 wearing the adaptive spectacles 10 is viewing and/or using the display screen 16, the controller 15 is configured to: determine the relative position; perform other calculations described above; and prepare the command signal, based on the relative position, for sending to the adaptive spectacles 10 to adjust the focus aspect(s) of the electrically-tunable lens(es) 22, 24.

The interface 30 of the adaptive spectacles 10 is configured to receive the command signal from the device 12. If the command signal does not include the indication of the refractive power(s) to which the electrically-tunable lens(es) 22, 24 should be adjusted, the control circuitry 26 of the adaptive spectacles 10 is configured to calculate, based on the relative position and the given visual accommodation capability of the person, the refractive power(s) to which the electrically-tunable lens(es) 22, 24 will be adjusted. If the command signal does not include the indication of the optical center(s) 27 to which the electrically-tunable lenses 22, 24 should be adjusted, the control circuitry 26 is configured to calculate the optical center(s) 27 of the electrically-tunable lens(es) 22, 24 based on the relative position so that the line-of-sight 32 of the person 11 wearing the adaptive spectacles 10, and viewing the display screen 16, is aligned with the optical center(s) 27 of the electrically-tunable lens(es) 22, 24 when the electrically-tunable lens(es) 22, 24 will be adjusted.

The control circuitry 26 of the adaptive spectacles 10 is configured to adjust, based on the command signal, the focus aspect(s) of the electrically-tunable lens(es) 22, 24, such as the refractive power(s) of the electrically-tunable lens(es) 22, 24, and/or the optical center(s) 27 of the electrically-tunable lens(es) 22, 24 to align the line-of-sight 32 of the person 11 wearing the adaptive spectacles 10, and viewing the display screen 16, with the optical center(s) 27 of the electrically-tunable lens(es) 22, 24.

Precise detection of viewing distance, from the adaptive spectacles 10 to the display screen 16, by sensor 19 can be difficult and uncertain, and erroneous setting of the focal powers of lenses 22 and 24 can be disturbing to the person 11 wearing the adaptive spectacles 10. To alleviate this problem, should it arise, the electrically-tunable lenses 22 and 24 may be set to different, respective focal powers that bracket a certain target distance that is estimated based on the sensor 19. The lens power disparity takes advantage of the fact that binocular vision often requires only one eye to see a sharply-focused image in order for the view to seem focused. For example, if sensor 19 indicates that the target distance is 25 cm, for which electrically-tunable lenses 22 and 24 should be set to 3 diopters (relative to the person 11 normal refractive corrections), and the person 11 has a tolerance for defocus of 0.2 diopters, then control circuitry 26 may set electrically-tunable lenses 22 and 24 to respective powers of 2.8 and 3.2 diopters. This focal bracketing gives the person 11 the ability to see in focus over a wider range of distances (corresponding to powers of 2.6 to 3.4 diopters), in case the detected distance was not accurate.

The electrically-tunable lenses 22 and 24 can be operated with different optical powers at all times or only under certain circumstances in which the object distance is uncertain. The difference between the focal powers of the left and right lenses (0.4 diopters in the example above) can be constant or vary as a function of several parameters, such as the level of confidence in the object distance detected by sensor 19; the probability distribution of the outputs of sensor 19; lighting conditions; the detected distance itself; and/or the preferences of the person 11.

In another embodiment, the electrically-tunable lens 22 and/or the electrically-tunable lens 24 may comprise two or more optical elements that apply different, respective focal powers to the incoming light that is incident on one or both of the eyes of the person 11. These optical elements may be configured to refract light of different polarizations, for example by orienting the electro-optical layers in the elements in orthogonal directions. This embodiment is described further hereinbelow with reference to FIG. 2. The electrically-tunable lenses 22 and 24 may be configured to operate on orthogonal polarizations in a similar manner.

As noted earlier, shifting the optical center 27 to the line-of-sight of the person 11 wearing the adaptive spectacles 10 may improve lens quality, particularly when the user is looking through an area near the edge of the lens. Erroneous shifts of the optical center 27, however, can result in poor user experience. In one embodiment, control circuitry 26 overcomes this problem by applying a predefined time lag when shifting the optical center(s) 27 in response to changes in the relative position. The optical center(s) 27 of the electrically-tunable lens(es) 22, 24 thus moves gradually in response to eye movements, until it reaches the optimal position. Gradual movements of the optical center(s) 27 that are slow enough not to be noticeable by the person 11 may produce a more natural experience for the person 11 compared to abrupt lens shifts. The optical center(s) 27 of the electrically-tunable lenses 22 and 24 can be moved either simultaneously or consecutively, whether gradually or instantaneously in response to eye movements.

It should be noted that FIG. 1A has generally been described with reference to the mobile device 12. The systems and/or methods described above may also be implemented using any suitable device, for example, but not limited to a laptop, or a PC with an external monitor and an external sensor.

Eye Therapy

As discussed above, some people suffer from limited accommodation capability and can benefit from special therapy. Such therapy includes training sessions forcing the patient to accommodate—for example, by displaying a stereoscopic 3D image on a 3D computer screen. These treatments also make use of refractive lenses aiming to shift the focal distance and challenge the patient's accommodation system. These treatments use continuous changes of the stimuli so as to trigger the patient's eyes to change their accommodation continuously for a certain amount of time, resulting in improvement of the accommodation capability. Such eye therapy may be implemented using the adaptive spectacles 10 in conjunction with a PC, mobile phone, tablet device or other computing platform running the eye therapy session and controlling the adaptive spectacles 10 either wirelessly or via a tethered connection.

The controller 15 or another processer (not shown) of the mobile device 12 is configured to execute an eye therapy software application to display a plurality of images on the display screen 16. The plurality of images are generated to challenge a visual accommodation capability of the person 11. The eye therapy software application is configured to determine a given visual accommodation capability to which the person 11 is to be challenged. Alternatively, the visual accommodation capability to which the person 11 is to be challenged may be determined by the person 11 or an eye therapist or other health professional. The controller 15 is configured to calculate at least one refractive power to which the electrically-tunable lens(es) 22, 24 will be adjusted based on the relative position (based on the input from the sensor 19) and the given visual accommodation capability to which the person 11 is to be challenged. The controller 15 is configured to prepare a command signal to include the refractive power(s) to which the electrically-tunable lens(es) 22, 24 will be adjusted. The adaptive spectacles 10 are configured to adjust the refractive power(s) of the electrically-tunable lens(es) 22, 24 according to the received command signal. Eye therapy may also be implemented using a VR headset, displaying the images at varying virtual distances, to trigger different accommodation reflex reactions, and controlling the adaptive spectacles 10 (installed inside the VR headset) to change focus according to the treatment plan.

In practice, some or all of the functions of the controller 15 may be combined in a single physical component or, alternatively, implemented using multiple physical components. These physical components may comprise hard-wired or programmable devices, or a combination of the two. In some embodiments, at least some of the functions of the processing circuitry may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

As mentioned above, the adaptive spectacles 10 may also be used to implement eye testing to determine a prescription for vision correction. For example, optometrists may use a display screen in the examination room (typically installed on a wall at least 3 meters away from the patient) while the patient is wearing the adaptive spectacles 10. The patient, or optometrist, controls the optical power applied to the tunable lenses 22, 24, and the optical center of the tunable lenses 22, 24 is automatically controlled so that the center of the tunable lenses 22, 24 is aligned with the line-of-sight between the patient and the display screen. The optical power of the tunable lenses 22, 24 may be controlled by the patient, or optometrist via a user input directly to the adaptive spectacles 10 or to the adaptive spectacles 10 via a remote device such as the mobile device 12. The optical power of the tunable lenses 22, 24 may be received by the controller 15 and/or the control circuitry 26.

Similar tests can be conducted for determining a prescription for presbyopia with the patient (or optometrist) holding the mobile device 12 at a distance of 30-40 cm away from the patient's eyes while tuning the refractive power of the spectacles 10, and controlling the optical center of the tunable lens 22, 24 to be aligned automatically with the line-of-sight between the patient and the screen 16 of the mobile device 12.

Vehicle Control

Figure 1B:
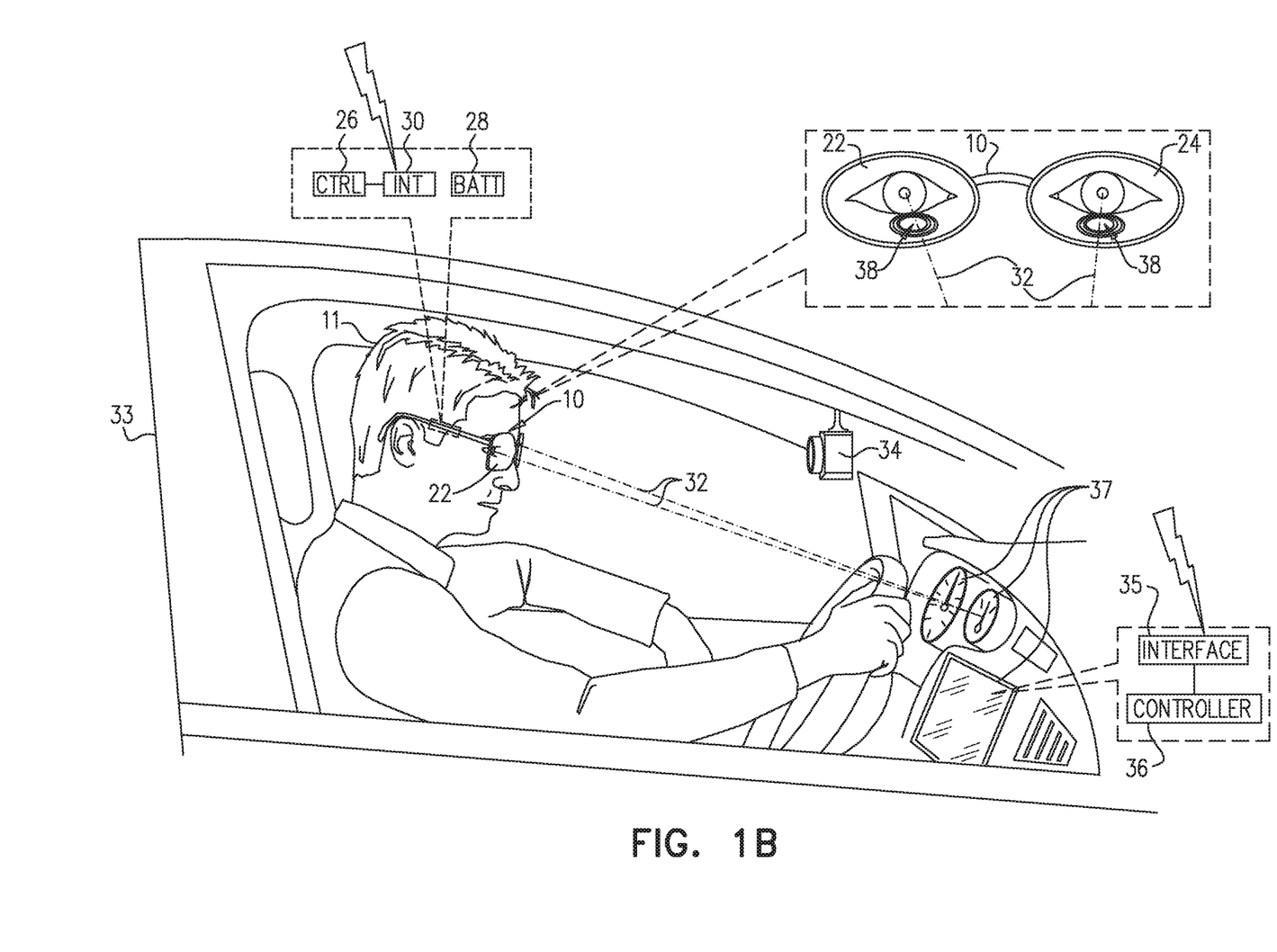
FIG. 1B is a schematic, pictorial illustration of the adaptive spectacles of FIG. 1A being used while driving a vehicle in accordance with another embodiment of the present invention.

Reference is now made to FIG. 1B, which is a schematic, pictorial illustration of the adaptive spectacles 10 of FIG. 1A being used while driving a vehicle 33 in accordance with another embodiment of the present invention.

As discussed above, when driving, people have to continuously change their vision focus from far distances, when looking at the road, to close distance when looking at a vehicle instrument panel 37 (e.g., car gauges and possibly one or more other display screens). For people with presbyopia, this is a difficult task and vision quality is poor.

The vehicle 33 includes a sensor 34 (performing a similar function to the sensor 19 of FIG. 1A), which may be implemented as part of a driver gaze detection system in the vehicle 33. Examples of such systems can be found in existing car and truck models—designed to detect and alert for driver fatigue or distraction. The vehicle 33 includes an interface 35 and a controller 36. The interface 35 and the controller 36 perform similar functions to the interface 17 and the controller 15 of FIG. 1A, respectively. The sensor 34, generally in conjunction with the controller 36, calculates the relative position of the adaptive spectacles 10 with respect to the vehicle instrument panel 37. The controller 36 prepares a command signal for sending to the adaptive spectacles 10 via the interface 35 for the adaptive spectacles 10 to adjust the focus aspect(s) of the electrically-tunable lens(es) 22, 24. The focus aspect(s) may include a refractive power(s) and/or an optical center(s) 38 of the electrically-tunable lenses 22 and 24 as discussed in more detail above with reference to FIG. 1A. The command signal is prepared in a similar manner as described above with reference to FIG. 1A.

The refractive power(s) and the optical centers 38 of the electrically-tunable lens(es) 22, 24 are generally adjusted if the controller 36 determines that the person 11 is looking down at the vehicle instrument panel 37 which may be based on the controller 36 analyzing an eye gaze direction of the person 11 captured by the sensor 34 or determining that part of the vehicle instrument panel 37 is being touched (e.g., a touch sensitive screen of the vehicle instrument panel 37). Therefore, in response to the controller 36 determining that the person 11 wearing the adaptive spectacles 10 is viewing or using the vehicle instrument panel 37, the controller 36 is configured to determine the relative position of the adaptive spectacles 10 with respect to the vehicle instrument panel 37 and prepare the command signal, based on the relative position, for sending to the adaptive spectacles 10 to adjust the focus aspect(s) of the electrically-tunable lens(es) 22, 24. In response to receiving the command signal via the interface 30, the control circuitry 26 of the adaptive spectacles 10 is configured to adjust the refractive power(s) and the optical centers 38 of the electrically-tunable lens(es) 22, 24.

When driving, for safety reasons, it may be beneficial to make sure a significant part of the electrically-tunable lenses 22 and 24, typically the top parts, will constantly stay focused to far distance. In such cases, when the controller 36 identifies that the person 11 requires vision correction for close distances, the positive lenses may be realized on only a part of the panels of the electrically-tunable lenses 22 and 24, for example using techniques described in the above PCT International Publication WO 2015/186010.

Detailed Features of Electrically-Tunable Lenses

Figure 2:
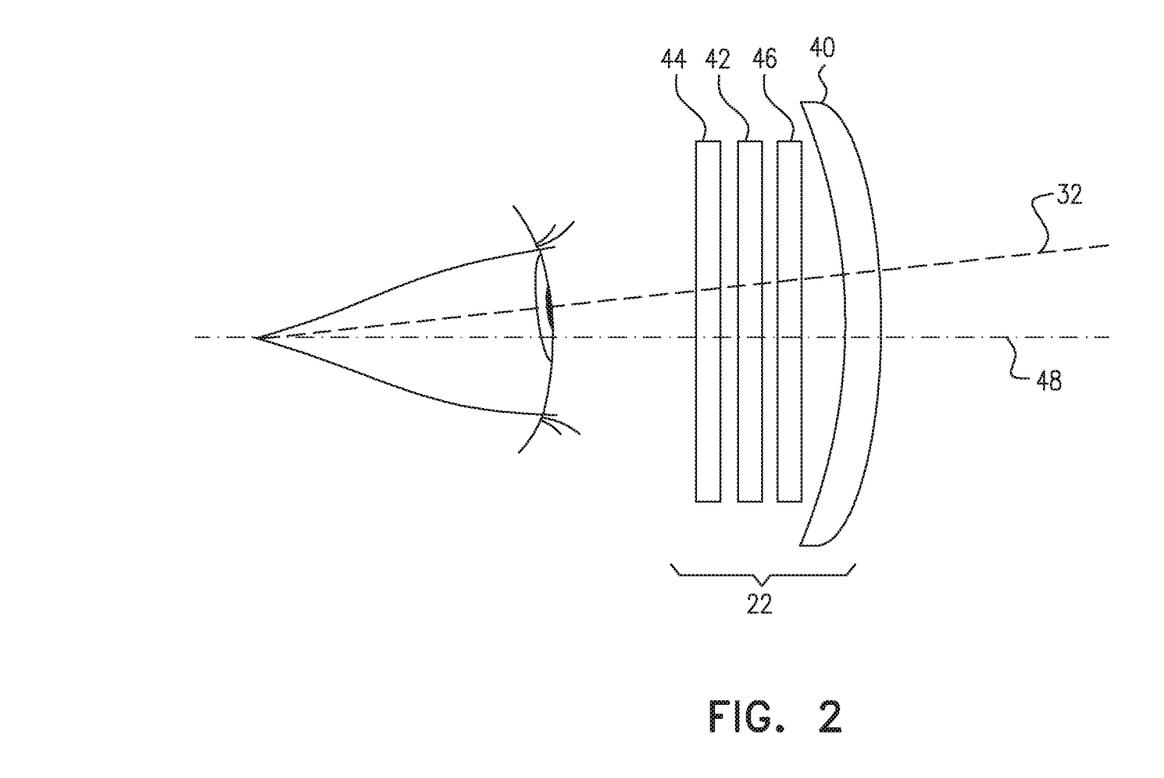
FIG. 2 is a schematic side view of an electrically-tunable lens system, in accordance with an embodiment of the invention.

Reference is now made to FIG. 2, which is a schematic side view of electrically-tunable lens 22, in accordance with an embodiment of the invention. Lens 24 is typically of similar design.

In the pictured embodiment, lens 22 is a compound lens, which comprises multiple elements: A fixed lens 40, typically made from glass or plastic, provides a baseline optical power, which is modified dynamically by two electrically-tunable lenses 42 and 44. For this reason, lens 22 itself can be considered an electrically-tunable lens. Alternatively, lens 22 may comprise only a single electrically-tunable element, and fixed lens 40 may not be needed in some applications. In some embodiments, lens 22 also comprises a polarizing element 46, such as a polarizer and/or polarization rotator, with functionality as described hereinbelow. The elements included in the lens 22 as shown in FIG. 2 may be positioned differently. For example, the polarizing element 46 may be positioned between tunable lens 44 and the eye, or alternatively farthest from the eye, on the outer surface of the fixed lens 40. Furthermore, the fixed lens 40 can be divided into two fixed lenses, one positioned nearest to the eye and one positioned farthest from the eye, thus enclosing the tunable lenses 42, 44 within the fixed lens.

Electrically-tunable lenses 42 and 44 adjust the optical power of lens 22 depending on the focal distance to the object being viewed by the user, while taking into account the considerations described in the preceding section. Additionally, or alternatively, an optical center 48 of lenses 42 and 44 may be shifted in response to changes in gaze direction 32, as was likewise described above. Lenses 42 and 44 may comprise electrically-tunable cylindrical lenses, with orthogonal cylinder axes. Alternatively, lenses 42 and 44 may be configured, as shown in FIGS. 3A-3D, to generate two-dimensional phase modulation profiles and thus emulate spherical or aspheric lenses (or their Fresnel equivalents). Both of these sorts of lens configurations, as well as waveforms for driving the lenses, are described in detail in the above-mentioned WO 2014/049577.

As noted earlier, in some embodiments in which lenses 42 and 44 comprise respective polarization-dependent electro-optical layers, the two lenses are oriented so as to refract mutually-orthogonal polarizations: One of these lenses, for example, lens 42, operates on light polarized in the X-direction (pointing into the page in the view shown in FIG. 2), and does not influence light polarized in the Y-direction (pointing upward in this view). Lens 44 operates on light polarized in the Y-direction, possibly with a different focal length from lens 42, and does not influence light polarized in the X-direction. Unpolarized light passing through lenses 42 and 44 will thus be focused at both distances, with roughly half the light focused according to the focal length of lens 42, while the other half is focused according to the focal length of lens 44.

This solution may not work when there is polarized light in the optical path. In such a case, if the light is polarized in the same direction as one of lenses 42 and 44, then all of the light will be focused according to the focal length of that lens.

To avoid this sort of polarization-dependence, in some embodiments polarizing element 46 comprises a polarization rotator, for example as described in the above-mentioned PCT publication WO 2015/186010, which intercepts the incoming light and rotates its polarization so as to ensure that the light incident on the electro-optical layers of lenses 42 and 44 has a component at each of the respective polarizations, regardless of the initial polarization of the intercepted light.

In some embodiments, the lens 22 may include two electrically-tunable cylindrical lenses 42 and two electrically-tunable cylindrical lenses 44, with orthogonal cylinder axes, so that two of the lenses 42 are aligned with one common cylindrical axis and two of the lenses 44 are aligned with the other orthogonal cylindrical axis. Additionally, the lenses 42 include one lens which operates on light polarized in the X-direction and one which operates on light polarized in the Y-direction. Similarly, the lenses 44 include one lens which operates on light polarized in the X-direction and one which operates on light polarized in the Y-direction.

Figure 3A:
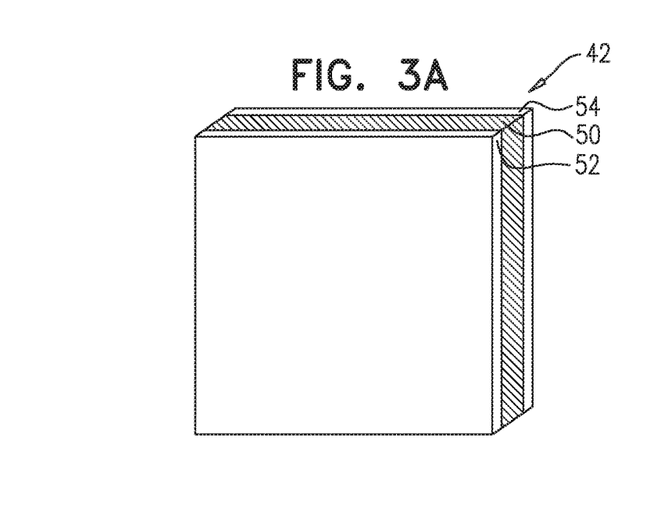
FIG. 3A is a schematic, pictorial illustration of an electrically-tunable lens, in accordance with another embodiment of the present invention.
Figure 3B:
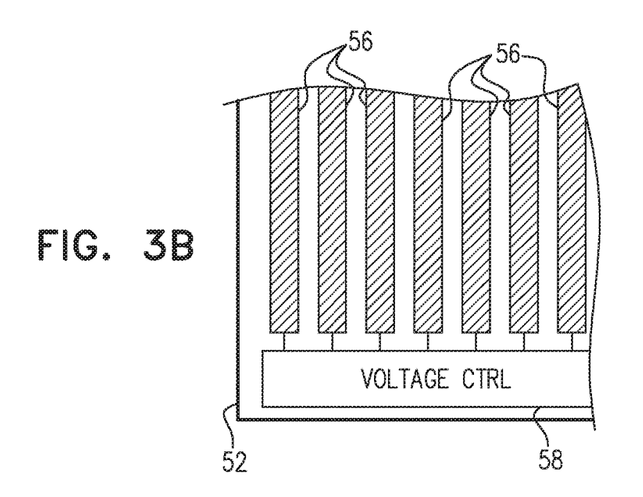
FIGS. 3B and 3C are schematic frontal views of electrodes formed on opposing sides of the lens of FIG. 3A, in accordance with an embodiment of the present invention.
Figure 3C:
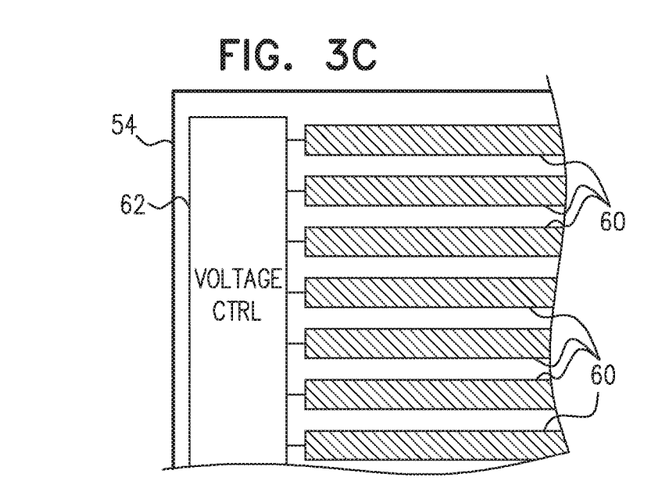
Figure 3D:
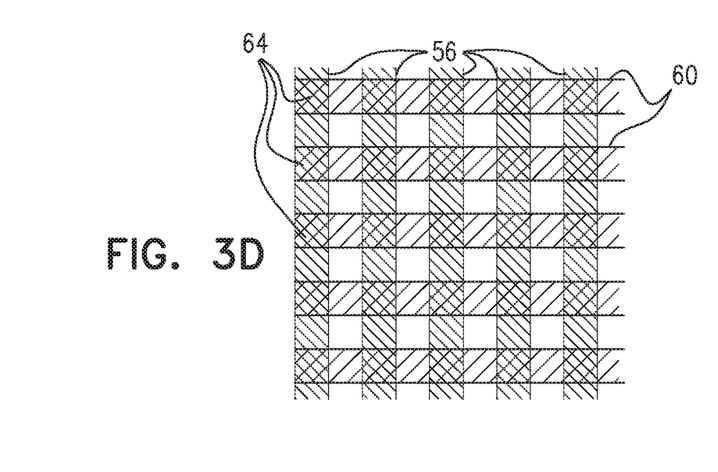
FIG. 3D is a schematic frontal of the lens of FIG. 3A, showing a superposition of the electrodes on the opposing sides of the lens, in accordance with an embodiment of the present invention.

FIGS. 3A-3D schematically show details of electrically-tunable lens 42 in accordance with an embodiment of the present invention. FIG. 3A is a pictorial illustration of lens 42, while FIGS. 3B and 3C are side views showing transparent substrates 52 and 54 on opposing sides of an electro-optical layer 50 in lens 42. FIG. 3D is a side view of device 42, showing a superposition of excitation electrodes 56 and 60 that are located on substrates 52 and 54 on the opposing sides of lens 42. Lens 44 may be of similar design. The lenses of FIGS. 2 and 3A-D are exemplary lenses which may be used with the adaptive spectacles 10. Any other suitable electrically-tunable lenses may be used with the adaptive spectacles 10.

Electro-optical layer 50 typically comprises a liquid-crystal layer, as described in the above-mentioned PCT International Publication WO 2014/049577. As explained above, layer 50 typically refracts light, in response to the voltage waveforms applied by electrodes 56 and 60, in only one direction of polarization, while the other polarization passes through lens 42 without refraction. Alternatively, layer 50 may comprise a cholesteric liquid crystal or other electro-optical material that is polarization-independent.

Electrodes 56 and 60 on substrates 52 and 54, respectively, comprise parallel stripes of transparent conductive material extending over the active area of layer 50 in mutually-orthogonal directions. Although electrodes 56 and 60 are of uniform shape and spacing in the figures, the stripes may alternatively have varying sizes and/or pitch. As shown in FIG. 3D, the superposition of electrodes 56 and 60 creates an array of pixels 64, defined by the areas of overlap of the vertical stripes of electrodes 56 with the horizontal stripes of electrodes 60.

Control circuits 58 and 62, under the control of control circuitry 26 or another controller, apply control voltages to excitation electrodes 56 and 60, respectively. As described in the above-mentioned WO 2014/049577, the control circuits in lens 42 are able to modify the control voltages applied to each of a set of the excitation electrodes (which may include all of the electrodes) simultaneously and independently. Control circuits 58 and 62 together can modify the voltages applied to sets of the excitation electrodes on both of the sides of layer 50, thereby modifying the phase modulation profile of the layer in two dimensions.

The control voltages applied to excitation electrodes 56 and 60 tune the focal properties of lens 42, as determined by the phase modulation profile. Control circuits 58 and 62 can modify the control voltages so as to change the focal length and/or to shift the optical center of the lens. The voltage patterns applied by circuits 58 and 62 across electrodes 56 and 60 may be chosen so as to give a phase modulation profile that is circularly symmetrical, and may thus emulate a spherical or aspheric lens. Alternatively, different voltage patterns may be applied so that lens 42 functions, for example, as an astigmatic lens, with a stronger cylindrical component along one axis or the other.

Partitioned Dynamic Lenses

In some cases, it may be desirable to partition the area of an electrically-tunable lens, such as lenses 22 and 24, into two independent lenses. For example, adaptive spectacles 10 may be configured so that in some scenarios, the lenses are partitioned, with part of the lenses set constantly for the user's vision correction to infinity, and the other part changing dynamically. Various examples that support optional spatial partitioning of the area of an electrically-tunable lens are described in the above-mentioned PCT publication WO 2015/186010. The lens in those examples can be operated as a single lens spanning over all (or at least part) of the active area, or the active area can be partitioned into two or more regions, each region implementing different lens characteristics (such as focal length and/or optical center). The lenses can be made to switch dynamically between these modes.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The present invention is not limited by what has been particularly shown and described hereinabove. Rather the scope of the invention is defined by the appended claims and equivalents thereof.

What is claimed is:

1. A system for controlling at least one focus aspect of adaptive spectacles having at least one electrically-tunable lens, the system comprising:
   a housing, which is physically separate from the adaptive spectacles;
   a display screen mounted in the housing and configured to be viewed through the adaptive spectacles by a person;

a sensor mounted in the housing and configured to detect a relative position of the adaptive spectacles with respect to the display screen;
an interface configured to communicate with the adaptive spectacles; and
a controller configured to:
receive an input signal from the sensor, the input signal being indicative of the relative position of the adaptive spectacles with respect to the display screen; and
output, in response to the input signal, a command signal for sending to the adaptive spectacles via the interface to adjust the at least one focus aspect of the at least one electrically-tunable lens, wherein the command signal is indicative of an optical center of the at least one electrically-tunable lens to which the at least one electrically-tunable lens is to be adjusted in order to align a line-of-sight of the person wearing the adaptive spectacles and viewing the display screen with the optical center of the at least one electrically-tunable lens.

2. The system according to claim 1, wherein the command signal is indicative of at least one refractive power to which the at least one electrically-tunable lens will be adjusted.

3. The system according to claim 2, wherein the controller is configured to calculate, based on the relative position, the at least one refractive power to which the at least one electrically-tunable lens will be adjusted.

4. The system according to claim 3, wherein the controller is configured to calculate the at least one refractive power, based on the relative position and a given visual accommodation capability of the person wearing the adaptive spectacles.

5. The system according to claim 3, further comprising the adaptive spectacles, the adaptive spectacles being configured to receive the command signal and adjust the at least one electrically-tunable lens to provide the at least one refractive power.

6. The system according to claim 1, wherein the controller is configured to calculate the optical center of the at least one electrically-tunable lens based on the relative position so that the line-of-sight of the person wearing the adaptive spectacles and viewing the display screen is aligned with the optical center of the at least one electrically-tunable lens when the at least one electrically-tunable lens will be adjusted.

7. The system according to claim 6, further comprising the adaptive spectacles, the adaptive spectacles being configured to receive the command signal and adjust the optical center of the at least one electrically-tunable lens to align the line-of-sight of the person wearing the adaptive spectacles and viewing the display screen with the optical center of the at least one electrically-tunable lens.

8. The system according to claim 1, wherein the interface, the controller, the sensor, and the display screen are implemented in a mobile device.

9. The system according to claim 8, wherein:
the sensor includes a front-facing camera disposed adjacent to the display screen; and
the controller is configured to determine the relative position of the adaptive spectacles with respect to the display screen based on image analysis of images captured by the front-facing camera of the mobile device.

10. The system according to claim 8, wherein the sensor includes a depth-sensor.

11. The system according to claim 1, wherein, the controller is configured to:

determine when the person wearing the adaptive spectacles is viewing or using the display screen; and
in response to determining that the person wearing the adaptive spectacles is viewing or using the display screen: determine the relative position; and prepare the command signal, based on the relative position, for sending to the adaptive spectacles to adjust the at least one focus aspect of the at least one electrically-tunable lens.

12. The system according to claim 11, wherein the controller is configured to determine when the person wearing the adaptive spectacles is viewing the display screen based on analyzing an eye gaze direction of the person captured by the sensor.

13. The system according to claim 12, wherein the sensor is implemented as part of a vehicle gaze detection system and the display screen is implemented as part of a vehicle instrument panel.

14. The system according to claim 11, wherein the controller is configured to determine when the person wearing the adaptive spectacles is using the display screen based on user interaction with a touch sensitive portion of the display screen.

15. The system according to claim 1, wherein: the interface is configured to receive an orientation reading from the adaptive spectacles; and the controller is configured to correct the relative position based on the orientation reading.

16. The system according to claim 1, further comprising a processor configured to execute an eye therapy software application to display a plurality of images on the display screen, the plurality of images being generated to challenge a visual accommodation capability of the person, wherein the controller is configured to: calculate at least one refractive power to which the at least one electrically-tunable lens will be adjusted based on the relative position and a given visual accommodation capability to which the person is to be challenged; and prepare the command signal to include the at least one refractive power to which the at least one electrically-tunable lens will be adjusted.

17. A system for controlling adaptive spectacles, the system comprising:
a mobile device including: a housing, which is physically separate from the adaptive spectacles; a display screen mounted in the housing and configured to be viewed through the adaptive spectacles by a person; a sensor mounted in the housing and configured to detect a relative position of the adaptive spectacles with respect to the display screen; a first interface configured to communicate with the adaptive spectacles; and a controller configured to:
receive an input signal from a sensor, the input signal being indicative of the relative position of the adaptive spectacles with respect to the display screen; and
output in response to the input signal, a command signal for sending to the adaptive spectacles via the first interface; and
the adaptive spectacles including:
a spectacle frame;
at least one electrically-tunable lens mounted in the spectacle frame;
a second interface configured to receive the command signal from the mobile device; and
control circuitry configured to adjust the at least one focus aspect of the at least one electrically-tunable lens based on the command signal, wherein the command signal is indicative of an optical center of the at least one electrically-tunable lens to which the at least one electrically-tunable lens is to be adjusted in order to align a line-of-sight of the person wearing the adaptive spectacles and viewing the display screen with the optical center of the at least one electrically-tunable lens.

18. The system according to claim 17, wherein the command signal includes at least one refractive power to which the at least one electrically-tunable lens will be adjusted.

19. The system according to claim 17, wherein the control circuitry is configured to calculate, based on the relative position, at least one refractive power to which the at least one electrically-tunable lens will be adjusted.

20. The system according to claim 19, wherein the control circuitry is configured to calculate the at least one refractive power, based on the relative position and a given visual accommodation capability of the person.

21. The system according to claim 19, wherein the control circuitry is configured to adjust the at least one electrically-tunable lens to provide the at least one refractive power.

22. The system according to claim 17, wherein the control circuitry is configured to calculate an optical center of the at least one electrically-tunable lens based on the relative position so that a line-of-sight of the person wearing the adaptive spectacles and viewing the display screen is aligned with the optical center of the at least one electrically-tunable lens when the at least one electrically-tunable lens will be adjusted.

23. The system according to claim 22, wherein the control circuitry is configured to adjust the optical center of the at least one electrically-tunable lens to align the line-of-sight of the person wearing the adaptive spectacles and viewing the display screen with the optical center of the at least one electrically-tunable lens.

24. The system according to claim 17, wherein: the first interface is configured to receive an orientation reading from the adaptive spectacles; and the controller is configured to correct the relative position based on the orientation reading.

25. A system for managing eye therapy via at least one focus aspect of adaptive spectacles having at least one electrically-tunable lens, the system comprising:
an interface configured to communicate with the adaptive spectacles;
a processor configured to execute an eye therapy software application to display a plurality of images on a display screen, the plurality of images being generated to challenge a visual accommodation capability of the person; and
a controller configured to:
calculate at least one refractive power to which the at least one electrically-tunable lens will be adjusted at least based on a given visual accommodation capability to which the person is to be challenged; and
output, to the adaptive spectacles via the interface, a command signal including the at least one refractive power to which the at least one electrically-tunable lens will be adjusted.

26. A method for controlling at least one focus aspect of adaptive spectacles having at least one electrically-tunable lens, the method comprising:
detecting, using a sensor, a relative position of the adaptive spectacles with respect to a display screen configured to be viewed through the adaptive spectacles by a person, the display screen being mounted in a housing with the sensor, the housing being physically separate from the adaptive spectacles;
communicating with the adaptive spectacles;
receiving an input signal from the sensor indicative of the relative position of the adaptive spectacles with respect to the display screen; and
outputting, in response to the input signal, a command signal for sending to the adaptive spectacles to adjust the at least one focus aspect of the at least one electrically-tunable lens, wherein the command signal is indicative of an optical center of the at least one electrically-tunable lens to which the at least one electrically-tunable lens is to be adjusted in order to align a line-of-sight of the person wearing the adaptive spectacles and viewing the display screen with the optical center of the at least one electrically-tunable lens.

27. The method according to claim 26, wherein the command signal is indicative of at least one refractive power to which the at least one electrically-tunable lens will be adjusted.

28. The method according to claim 26, further comprising calculating, based on the relative position, at least one refractive power to which the at least one electrically-tunable lens will be adjusted.

29. The method according to claim 26, further comprising calculating at least one refractive power, based on the relative position and a given visual accommodation capability of the person wearing the adaptive spectacles.

30. The method according to claim 26, further comprising calculating an optical center of the at least one electrically-tunable lens based on the relative position so that a line-of-sight of the person wearing the adaptive spectacles and viewing the display screen is aligned with the optical center of the at least one electrically-tunable lens when the at least one electrically-tunable lens will be adjusted.

31. The method according to claim 26, further comprising determining the relative position of the adaptive spectacles with respect to the display screen based on image analysis of images captured.

32. The method according to claim 26, further comprising:
determining when the person wearing the adaptive spectacles is viewing or using the display screen; and
in response to determining that the person wearing the adaptive spectacles is viewing or using the display screen: determining the relative position; and preparing the command signal, based on the relative position, for sending to the adaptive spectacles to adjust the at least one focus aspect of the at least one electrically-tunable lens.

33. The method according to claim 32, further comprising determining when the person wearing the adaptive spectacles is viewing the display screen based on analyzing an eye gaze direction of the person captured by the sensor.

34. The method according to claim 32, further comprising determining when the person wearing the adaptive spectacles is using the display screen based on user interaction with a touch sensitive portion of the display screen.

35. The method according to claim 26, further comprising:
executing an eye therapy software application to display a plurality of images on the display screen, the plurality of images being generated to challenge a visual accommodation capability of the person;
calculating at least one refractive power to which the at least one electrically-tunable lens will be adjusted based on the relative position and a given visual accommodation capability to which the person is to be challenged; and preparing the command signal to include the at least one refractive power to which the at least one electrically-tunable lens will be adjusted.

36. A method for controlling adaptive spectacles, the method comprising:
    performing in a mobile device comprising a housing which houses a sensor and a display screen:
        detecting, using the sensor, a relative position of the adaptive spectacles with respect to the display screen configured to be viewed through the adaptive spectacles by a person, the housing being physically separate from the adaptive spectacles;
        communicating with the adaptive spectacles;
        receiving an input signal indicative of the relative position of the adaptive spectacles with respect to the display screen; and
        outputting, in response to the input signal, a command signal for sending to the adaptive spectacles to adjust the at least one focus aspect of the at least one electrically-tunable lens; and
    the adaptive spectacles adjusting the at least one focus aspect of at least one electrically-tunable lens of the adaptive spectacles based on the command signal, wherein the command signal is indicative of an optical center of the at least one electrically-tunable lens to which the at least one electrically-tunable lens is to be adjusted in order to align a line-of-sight of the person wearing the adaptive spectacles and viewing the display screen with the optical center of the at least one electrically-tunable lens.

37. The method according to claim 36, wherein the command signal includes at least one refractive power to which the at least one electrically-tunable lens will be adjusted.

38. The method according to claim 36, further comprising calculating, based on the relative position, at least one refractive power to which the at least one electrically-tunable lens will be adjusted.

39. The method according to claim 38, further comprising adjusting the at least one electrically-tunable lens to provide the at least one refractive power.

40. The method according to claim 36, further comprising calculating at least one refractive power, based on the relative position and a given visual accommodation capability of the person.

41. The method according to claim 36, further comprising calculating an optical center of the at least one electrically-tunable lens based on the relative position so that a line-of-sight of the person wearing the adaptive spectacles and viewing the display screen is aligned with the optical center of the at least one electrically-tunable lens when the at least one electrically-tunable lens will be adjusted.

42. The method according to claim 41, further comprising adjusting the optical center of the at least one electrically-tunable lens to align the line-of-sight of the person wearing the adaptive spectacles and viewing the display screen with the optical center of the at least one electrically-tunable lens.

43. A method for managing eye therapy via at least one focus aspect of adaptive spectacles having at least one electrically-tunable lens, the method comprising:
    communicating with the adaptive spectacles;
    executing an eye therapy software application to display a plurality of images on a display screen, the plurality of images being generated to challenge a visual accommodation capability of the person;
    calculating at least one refractive power to which the at least one electrically-tunable lens will be adjusted at least based on a given visual accommodation capability to which the person is to be challenged; and
    outputting, to the adaptive spectacles via the interface, a command signal including the at least one refractive power to which the at least one electrically-tunable lens will be adjusted.

44. A software product, comprising a non-transient computer-readable medium in which program instructions are stored, which instructions, when read by a central processing unit (CPU), cause the CPU to:
    receive an input signal from a sensor, the input signal being indicative of a relative position of adaptive spectacles with respect to a display screen, which is configured to be viewed through the adaptive spectacles by a person, the display screen being mounted in a housing with the sensor, the housing being physically separate from the adaptive spectacles; and
    output, in response to the input signal, a command signal for sending to the adaptive spectacles to adjust the at least one focus aspect of at least one electrically-tunable lens of the adaptive spectacles, wherein the command signal is indicative of an optical center of the at least one electrically-tunable lens to which the at least one electrically-tunable lens is to be adjusted in order to align a line-of-sight of the person wearing the adaptive spectacles and viewing the display screen with the optical center of the at least one electrically-tunable lens.

45. A software product, comprising a non-transient computer-readable medium in which program instructions are stored, which instructions, when read by a central processing unit (CPU), cause the CPU to:
    communicate with adaptive spectacles having at least one electrically-tunable lens;
    execute an eye therapy software application to display a plurality of images on a display screen, the plurality of images being generated to challenge a visual accommodation capability of the person;
    calculate at least one refractive power to which the at least one electrically-tunable will be adjusted at least based on a given visual accommodation capability to which the person is to be challenged; and
    output, to the adaptive spectacles via an interface, a command signal including the at least one refractive power to which the at least one electrically-tunable lens will be adjusted.

* * * * *